United States Patent
Mizuno et al.

(10) Patent No.: US 8,344,167 B2
(45) Date of Patent: Jan. 1, 2013

(54) METHOD FOR PRODUCING PROPYLENE OXIDE

(75) Inventors: Masahiko Mizuno, Nara (JP); Hideo Narahara, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 311 days.

(21) Appl. No.: 12/667,967

(22) PCT Filed: Jul. 4, 2008

(86) PCT No.: PCT/JP2008/062538
§ 371 (c)(1),
(2), (4) Date: Jan. 6, 2010

(87) PCT Pub. No.: WO2009/008493
PCT Pub. Date: Jan. 15, 2009

(65) Prior Publication Data
US 2010/0197946 A1    Aug. 5, 2010

(30) Foreign Application Priority Data
Jul. 10, 2007   (JP) .................. 2007-180644

(51) Int. Cl.
*C07D 301/03* (2006.01)
*C07D 301/06* (2006.01)

(52) U.S. Cl. .................. 549/533; 549/523; 549/532

(58) Field of Classification Search .................. 549/523, 549/532, 533
See application file for complete search history.

(56) References Cited

U.S. PATENT DOCUMENTS

| 3,813,378 A | 5/1974 | Witte et al. |
| 2009/0264665 A1 | 10/2009 | Kawabata et al. |

FOREIGN PATENT DOCUMENTS

| DE | 2 127 776 | | 12/1972 |
| DE | 33 34321 A1 | | 4/1985 |
| EP | 0 890 572 A1 | | 1/1999 |
| EP | 1 489 074 A1 | | 12/2004 |
| EP | 1 602 651 A1 | | 12/2005 |
| EP | 1 967 518 A1 | | 12/2006 |
| EP | 1 967 518 A1 | | 9/2008 |
| JP | 2004-269379 A | | 9/2004 |

(Continued)

OTHER PUBLICATIONS

"Year 2001 The Next Generation Chemical Process Technology Development and Non-Halogen Chemistry Process Technology Development Result Reports", Mar. 2002, pp. 168-209, New Energy and Industrial Technology Development Organization (the consignment ahead: Japan Chemical Innovation Institute).

(Continued)

*Primary Examiner* — Taylor Victor Oh
(74) *Attorney, Agent, or Firm* — Foley & Lardner LLP

(57) ABSTRACT

A method is for producing propylene oxide, the method including the steps of: reacting hydrogen peroxide with propylene either in an acetonitrile solvent or in a mixture of solvents which include acetonitrile and water, in presence of a titanosilicate catalyst, whereby a reaction mixture containing propylene oxide is obtained; separating the reaction mixture obtained in the reacting into a gas and a reaction liquid; and distilling the reaction liquid obtained in the separating, whereby the reaction liquid is separated into a column top liquid containing propylene oxide, and a column bottom liquid including acetonitrile or a combination of acetonitrile and water, in combination with other steps. This enables industrially efficient production of propylene oxide with use of acetonitrile.

16 Claims, 1 Drawing Sheet

FOREIGN PATENT DOCUMENTS

| | | |
|---|---|---|
| JP | 2004-269380 A | 9/2004 |
| JP | 2004-285055 A | 10/2004 |
| WO | WO 2006/077183 A1 | 7/2006 |
| WO | WO 2007/074760 A | 7/2007 |

OTHER PUBLICATIONS

"Next Generation and Non-Halogen Chemistry Process Technology Development Result Report 2002", 2003, pp. 152-180, New Energy and Industrial Technology Development Organization (the consignment ahead: Japan Chemical Innovation Institute).

The International Search Report received in the corresponding International application PCT/JP2008/062538, dated Feb. 26, 2009, (4 pgs.).

The International Search Report received in the corresponding international application PCT/JP2008/062536, dated Feb. 26, 2006. (4 pgs.).

Clerici, et al., "Synthesis of Propylene Oxide from Propylene and Hydrogen Peroxide Catalyzed by Titanium Silicalite", Journal of Catalysis, vol. 129, 1991, pp. 159-167. (XP000577042).

Goor et al. "Hydrogen Peroxide" in Ullmann's Encyclopedia of Industrial Chemistry, 2007, p. 6, Wiley-VCH Verlag GmbH & Co. KGaA, Weinheim, Germany.

Kirk-Othmer "Hydrogen Peroxide" in Encyclopedia of Chemical Technology, 2001, pp. 6-7, vol. 13, Wiley-VCH Verlag GmbH & Co. KGaA, Weinheim, Germany.

Notice of Opposition EP Application No. 08778059.9 dated Aug. 3, 2012.

Richard H. Wiley et al., "The Chemistry of the Oxazolines", Chemical Review 44(3), (1949), pp. 447-476.

Vadim Yu Kukushkin et al., "Metal-mediated and metal-catalyzed hydrolysis of nitriles", Inorganica Chimica Acta 358 (2005), pp. 1-21.

Heath H. Herman et al., "The Enantiomeric Specificity of the Antihypertensive Activity of 1-(Phenylthio)-2-aminopropane, a Synthetic Substrate Analogue for Dopamine β-Monaoxygenase", J. Med. Chem. 1991, 34, pp. 1082-1085.

"11.6.2. Number and Sequencing of columns", Chemical Engineering Design, Coulson & Richardson's Chemical Engineering, vol. 6, $4^{th}$ ed. (2005), p. 517.

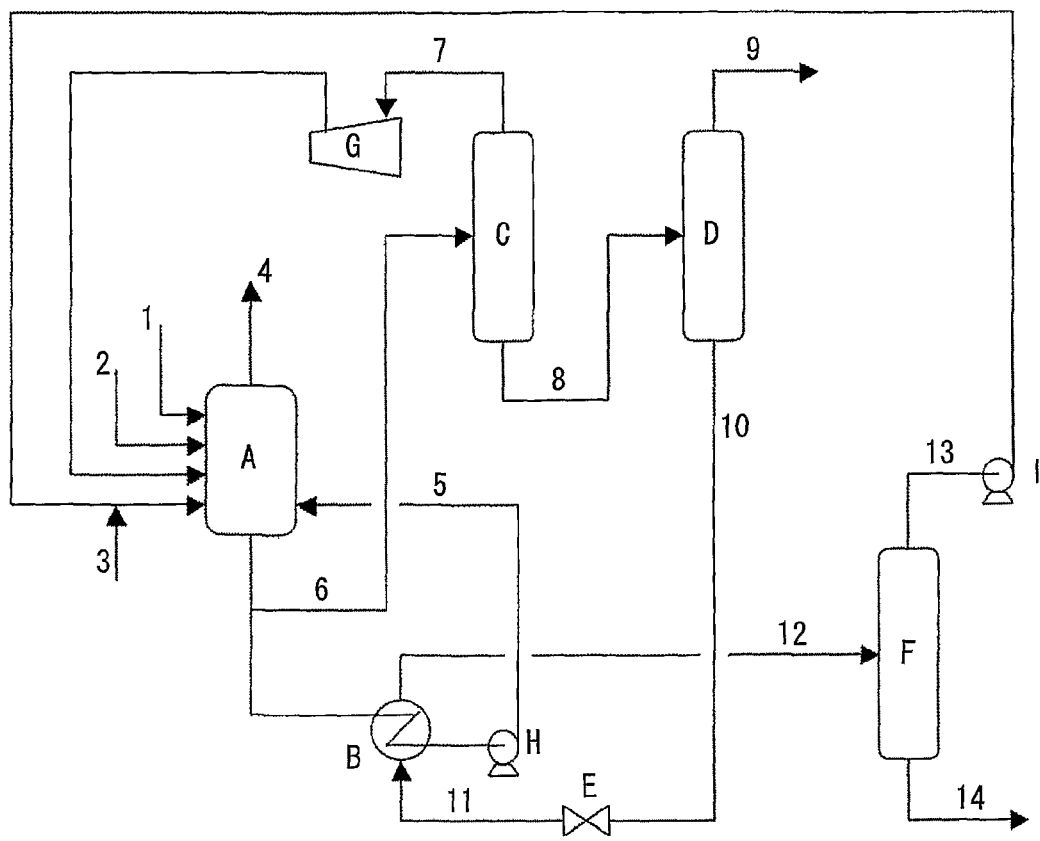

METHOD FOR PRODUCING PROPYLENE OXIDE

TECHNICAL FIELD

The present invention relates to a method for producing propylene oxide by reaction of hydrogen peroxide and propylene in an acetonitrile solvent, in presence of a titanosilicate catalyst.

BACKGROUND ART

There has been known a method for using an acetonitrile-water mixture as a solvent in production of propylene oxide from hydrogen peroxide and propylene, disclosed in "FY2001 Report of Development of Non-halogen Chemical Process Technology, pages 168 through 210; Development of Next-Generation Chemical Process Technology" and Japanese Unexamined Patent Application Publication No. 285055/2004 (Tokukai 2004-285055; published on Oct. 14, 2004). Further, there has been known a method for using an acetonitrile-water mixture as a solvent, synthesizing hydrogen peroxide from hydrogen and oxygen in a reactor, and reacting the hydrogen peroxide with propylene in the same reactor, disclosed in "FY2002 Report of Development of Non-halogen Chemical Process Technology, pages 161 and 175; Development of Next-Generation Chemical Process Technology" and Japanese Patent Application No. 345450/2006 (Tokugan 2006-345450).

DISCLOSURE OF INVENTION

It is an object of the present invention to provide an industrially efficient method for producing propylene oxide with use of acetonitrile.

A method of the present invention is for producing propylene oxide, the method including the steps of: reacting hydrogen peroxide with propylene either in an acetonitrile solvent or in a mixture of solvents which include acetonitrile and water, in presence of a titanosilicate catalyst, whereby a reaction mixture containing propylene oxide is obtained; separating the reaction mixture obtained in the reacting into a gas and a reaction liquid; and distilling the reaction liquid obtained in the separating, whereby the reaction liquid is separated into a distillate liquid containing propylene oxide, and a bottoms liquid including acetonitrile or a mixture of acetonitrile and water.

For a fuller understanding of the nature and advantages of the invention, reference should be made to the ensuing detailed description taken in conjunction with the accompanying drawing.

BRIEF DESCRIPTION OF DRAWING

FIG. 1 is a flowchart in accordance with an embodiment of the present invention.

DESCRIPTION OF THE CODES

| | |
|---|---|
| A | reactor |
| B | heat exchanger |
| C | gas-liquid separator |
| D | first distillation column |
| E | pressure control valve |
| F | second distillation column |
| G | compressor |
| H, I | pump |

BEST MODE FOR CARRYING OUT THE INVENTION

The following explains a reaction step. In the reaction step, propylene oxide is produced by reaction of hydrogen peroxide with propylene either in an acetonitrile solvent or in a mixture of solvents which include acetonitrile and water, in presence of a titanosilicate catalyst.

The propylene is produced by thermolysis, heavy oil catalytic cracking, or methanol catalytic reforming. The present invention permits use of either refined propylene or crude propylene. The propylene generally has a purity of 90% or greater by volume, and preferably 95% or greater by volume. The propylene may also include, other than propylene, propane, cyclopropane, methyl acethylene, propadiene, butadiene, butanes, butenes, ethylene, ethane, methane, or hydrogen, for example.

The propylene to be fed may be gaseous propylene or liquefied propylene; alternatively, liquefied propylene after being dissolved in a solvent. Preferably, liquefied propylene is fed; optionally after being dissolved in a solvent.

A method for producing the hydrogen peroxide is not particularly limited; preferably, an anthraquinone process or a method involving use of a noble metal catalyst. The hydrogen peroxide may be diluted by a dilution solvent. Generally, examples of the dilution solvent encompass water, a mixture of water and acetonitrile, and a mixture of water and alcohol, among which the water and the mixture of water and acetonitrile are preferable. The hydrogen peroxide generally has a concentration in a range from 0.1% to 80 wt %, and preferably in a range from 10% to 60 wt %. The hydrogen peroxide and the dilution solvent used therefor may include a stabilizer such as a phosphorus compound. Further, the hydrogen peroxide is preferably produced from hydrogen and oxygen with use of a palladium catalyst supported on a carrier in a same reactor as the propylene oxide is produced. An amount of the hydrogen peroxide is generally in a range from 0.005 to 10 mol, preferably in a range from 0.05 to 5 mol per mol of the propylene.

An acetonitrile-to-water weight ratio of the mixture of solvents which include acetonitrile and water is not particularly limited; for example, in a range from (i) 50:50 to (ii) 100:0. An amount of the acetonitrile solvent or the mixture of solvents which include acetonitrile and water is not particularly limited; for the sake of productivity, it is generally 20 g or less, preferably 10 g or less, and more preferably 5 g or less, for 1 mmol of the propylene feed.

The acetonitrile may be purified acetonitrile or crude acetonitrile generated in production of acrylonitrile as a byproduct; preferably, the purified acetonitrile is used. The acetonitrile used in the present invention generally has a purity of 95% or greater, and preferably 99% or greater; more preferably, 99.9% or greater. Further, the acetonitrile used in the present invention may include water, acetone, acrylonitrile, oxazole, allyl alcohol, propionitrile, hydrocyanic acid, ammonia, copper, and/or iron, for example.

The titanosilicate catalyst can be any porous silicate with part of Si thereof substituted by Ti; for example, crystalline titanosilicate, lamellar titanosilicate, or mesoporous titanosilicate. Examples of the crystalline titanosilicate encompass (i) TS-2 having MEL structure (according to the structure code of the International Zeolite Association (IZA); hereinafter the same applies), (ii) Ti-ZSM-12 having MTW structure (see Zeolites 15, 236-242 (1995)), (iii) Ti-Beta having BEA structure (see Journal of Catalysis 199, 41-47 (2001)), (iv) Ti-MWW having MWW structure (see Chemistry Letters, 774-775 (2000)), (v) Ti-UTD-1 having DON structure (see Zeolites 15, 519-525 (1995)), and (vi) TS-1 having MFI structure (see Journal of Catalysis, 130, (1991), 1-8). Examples of the lamellar titanosilicate encompass (i) a Ti-MWW precursor (see Japanese Unexamined Patent Application Publication No. 327425/2003 (Tokukai 2003-327425; published on Nov. 19, 2003)), and (ii) Ti-YNU (see Angewante Chemie International Edition 43, 236-240 (2004)). Examples of the mesoporous titanosilicate encompass (i) Ti-MCM-41 (see Microporous Material 10, 259-271 (1997)), (ii) Ti-MCM-48 (see Chemical Communications 145-146 (1996)), (iii) Ti-SBA-15 (see Chemistry of Materials 14, 1657-1664 (2002)), and (iv) Ti-MMM-1 (see Microporous and Mesoporous Materials 52, 11-18 (2002)). The crystalline titanosilicate and the lamellar titanosilicate preferably have a 12 or more-membered oxygen ring pore. Examples of the crystalline titanosilicate having a or more-membered oxygen ring pore encompass the Ti-ZSM-12, the Ti-MWW, and the Ti-UTD-1. Examples of the lamellar titanosilicate having a 12 or more-membered oxygen ring pore encompass the Ti-MWW precursor and the Ti-YNU; the more preferable thereof are the Ti-MWW and the Ti-MWW precursor.

The titanosilicate catalyst may be such that a silanol group thereof is silylated by a silylating agent. Examples of the silylating agent encompass 1,1,1,3,3,3-hexamethyldisilazane, trimethylsilyl chloride, and triethylsilyl chloride. The titanosilicate catalyst is generally pretreated with a solution of hydrogen peroxide before use. The solution of hydrogen peroxide has a concentration in a range from 0.0001 wt % to 50 wt %.

The reaction in the reaction step can be performed by such methods as a batch process, a slurry-bed continuous flow process, or a fixed-bed continuous flow process; among the above, the slurry-bed continuous flow process and the fixed-bed continuous flow process are preferable in terms of productivity.

According to the slurry-bed continuous flow process, the titanosilicate catalyst and the palladium catalyst supported on the carrier are filtered by a filter that is provided inside or outside the reactor, and then allowed to remain in the reactor. Subsequently, part of the catalysts contained in the reactor is continuously or intermittently withdrawn and then subjected to regeneration treatment. Thereafter, the reaction may be performed while the regenerated catalysts are resupplied to the reactor; alternatively, the reaction may be performed while part of the catalysts is withdrawn from the system, and the titanosilicate catalyst and the palladium catalyst supported on the carrier are newly fed to the reactor in an amount equivalent to an amount of the part of the catalysts withdrawn. The reactor contains the catalysts generally in an amount in a range from 0.01% to 20 wt % of a reaction liquid, and preferably in a range from 0.1% to 10 wt %.

According to the fixed-bed continuous flow process, the reaction is performed while reaction and regeneration are repeated alternately. In this case, the catalysts are preferably molded by a molding agent or the like.

A reaction temperature is generally in a range from 0° C. to 150° C., and preferably in a range from 20° C. to 100° C.; more preferably, in a range from 40° C. to 70° C. A reaction pressure is generally in a range from 0.1 to 20 MPa (absolute pressure), and preferably in a range from 1 to 10 MPa. In a case of performing the reaction in the same reactor as the hydrogen peroxide is produced from the hydrogen and the oxygen, the hydrogen, the oxygen, the propylene, and the acetonitrile solvent or the mixture of solvents which include acetonitrile and water are contained simultaneously in the reactor, and subsequently allowed to react in the presence of the titanosilicate catalyst and the palladium catalyst supported on the carrier, whereby the propylene oxide is produced.

Examples of the carrier that supports the palladium generally encompass (i) an oxide such as silica, alumina, titania, zirconia, and niobia, (ii) a hydrate such as niobic acid, zirconium acid, tungsten acid, and titanium acid, (iii) carbon as in activated carbon, carbon black, graphite, and carbon nanotube, and (iv) titanosilicate. A preferable carrier is the carbon or titanosilicate; more specifically, the activated carbon, Ti-MWW or Ti-MWW precursor is particularly preferable.

The palladium can be impregnated on the carrier after preparation of a palladium colloid solution; alternatively, the palladium salt is impregnated on the carrier after the palladium salt is dissolved in a solvent; alternatively, a palladium salt is dissolved in a solvent, with which the carrier is then impregnated. Examples of the palladium salt encompass palladium chloride, palladium nitrate, palladium sulfate, palladium acetate, and tetraamminepalladium chloride. In a case where the palladium is supported with use of the colloid solution, generally, the palladium catalyst supported on the carrier is preferably calcinated under an inert gas atmosphere. In a case where the palladium salt is used in supporting the palladium, generally, the palladium catalyst supported on the carrier is reduced by a reducing agent either in a liquid phase or in a gas phase before use. In a case where the tetraamminepalladium chloride is used, the palladium catalyst supported on the carrier may be reacted with ammonia that is generated by thermolysis of tetraammine palladium chloride, in the presence of an inert gas.

An amount of the palladium to be supported is generally in a range from 0.01% to 20 wt %, and preferably in a range from 0.1% to 5 wt %, of the palladium catalyst supported on the carrier. The palladium catalyst supported on the carrier may include one or more kinds of noble metals other than the palladium. Examples of the noble metal other than the palladium encompass platinum, ruthenium, rhodium, iridium, osmium, and gold. An amount of the noble metal other than the palladium to be included is not particularly limited.

General examples of the oxygen (in molecular form) encompass molecular oxygen purified by a cryogenic separation, molecular oxygen purified by a pressure swing adsorption (PSA), or air; preferable among the above are the molecular oxygen purified by the cryogenic separation and the molecular oxygen purified by the pressure swing adsorption. A feed of the oxygen is generally in a range from 0.005 to 10 mol, preferably in a range from 0.05 to 5 mol per mol of the propylene to be fed.

A method for producing the hydrogen is not particularly limited; for example, steam reforming of a hydrocarbon. Generally, the hydrogen has a purity of 80% or greater by volume, and preferably 90% by volume. A feed of the hydrogen is generally from 0.005 to 10 mol, preferably from 0.05 to 5 mol per mol of the propylene to be fed.

Generally, a gas feed for the reaction has a composition that is preferably out of an explosive range of the hydrogen and the propylene, for the sake of safety; thus, inclusion of a dilution gas is preferable for the reaction. Examples of the dilution gas encompass nitrogen gas, argon gas, methane gas, ethane gas, propane gas, and carbon dioxide gas. Among the above, the nitrogen gas and the propane gas are preferable; particularly preferable is the nitrogen gas. In a case where a concentration of the hydrogen is controlled so that the composition of the gas is out of the explosive range, the concentration of the hydrogen in the gas feed is generally required to be 3.9% or less by volume. In this case, a concentration of the oxygen is only required to be not greater than a limiting oxygen concentration of the propylene, i.e. generally, 11.5% or less by volume, and preferably 9% or less by volume. The dilution gas is fed so that such a composition of the gas feed is achieved. In a case where the concentration of the oxygen is controlled so that the composition of the gas is out of the explosive range, the concentration of the oxygen in the gas feed is generally required to be 4.9% or less by volume, and preferably 4% or less by volume. In this case, neither the concentration of the hydrogen nor a concentration of the propylene is particularly limited; generally, both of the concentrations are 10% or less by volume. The dilution gas is fed so that such a composition of the gas feed is achieved.

In the case of producing the hydrogen peroxide from the hydrogen and the oxygen, and reacting the hydrogen peroxide with the propylene in the same reactor, propylene oxide production having a better yield is realized preferably by adding (i) a mixture of one or more kinds of anthraquinone compounds, and (ii) a mixture of one or more kinds of ammonium salts. The anthraquinone compound and the ammonium salt may be used either solely or in combination.

The anthraquinone compound may be substituted anthraquinone, unsubstituted anthraquinone, or the like; preferably, the unsubstituted anthraquinone is used. Examples of the substituted anthraquinone encompass 2-ethylanthraquinone, 2-t-butylanthraquinone, 2-amylanthraquinone, 2-methylanthraquinone, 2-butylanthraquinone, 2-t-amylanthraquinone, 2-isopropylanthraquinone, 2-s-butylanthraquinone, 2-s-amylanthraquinone, 2-hydroxyanthraquinone, 1,3-diethylanthraquinone, 2,3-dimethylanthraquinone, 1,4-dimethylanthraquinone, 2,7-dimethylanthraquinone, and 2,6-dihydroxyanthraquinone.

The anthraquinone compound generally has a purity of 95% or greater, and preferably 98% or greater. The anthraquinone compound may include, other than the anthraquinone compound, an anthracene compound and a hydroanthraquinone compound, for example. The anthraquinone compound is generally dissolved in a solvent before being fed into the reactor. A lower limit of a feed of the anthraquinone compound is generally $1\times10^{-7}$ mol, preferably $1\times10^{-6}$ mol per mol of the propylene to be fed. An upper limit of the feed of the anthraquinone compound varies depending on solubility of the anthraquinone compound in the solvent; generally, it is 1 mol, preferably 0.1 mol per mol of the propylene to be fed.

Examples of the ammonium salt encompass ammonium sulfate, ammonium hydrogen sulfate, ammonium carbonate, ammonium hydrogencarbonate, ammonium dihydrogenphosphate, diammonium hydrogen phosphate, ammonium phosphate, ammonium hydrogen pyrophosphate, ammonium pyrophosphate, ammonium chloride, ammonium nitrate, and ammonium acetate. Among the above, the ammonium dihydrogenphosphate, diammonium hydrogen phosphate, ammonium phosphate is preferable.

The ammonium salt is generally dissolved in a solvent before being fed into the reactor. A lower limit of a feed of the ammonium salt is generally $1\times10^{-6}$ mol, preferably $1\times10^{-5}$ mol per mol of the propylene to be fed. An upper limit of the feed of the ammonium salt varies depending on solubility of the ammonium salt in the solvent; it is generally 2 mol, preferably 0.2 mol per mol of the propylene to be fed.

In a gas-liquid separation step, a reaction mixture is fed from the reactor to a gas-liquid separator in forms of a liquid and a gas, and then separated into a reaction liquid and a gas, under a pressure that is equal to or lower than the reaction pressure. The reaction liquid obtained by the separation includes an amide compound and an oxazoline compound, which are generated in the reaction step as a byproduct, as well as acetonitrile, propylene oxide, and water. Examples of the amide compound derived from the acetonitrile encompass acetamide, N-(2-hydroxypropan-1-yl)acetamide, and N-(1-hydroxypropan-2-yl)acetamide. Examples of the oxazoline compound encompass 2,4-dimethyloxazoline and 2,5-dimethyloxazoline.

Stable condition in a distillation column can be achieved when a flow rate and composition of the reaction liquid to be fed into the distillation column are stable. This allows stable production of propylene oxide without addition of an extra energy. In order to attain the stable condition in the distillation column, it is preferable to have a buffer tank between the gas-liquid separation step and a subsequent distillation step. A higher pressure inside the buffer tank requires the buffer tank to be undesirably large in thickness due to avoiding burst of buffer tank. Therefore, the pressure in the gas-liquid separation step is preferably lower than the reaction pressure.

The reaction liquid obtained as above is then fed into a first distillation column; distillation therein provides (i) crude propylene oxide, i.e. a distillate liquid containing propylene oxide and (ii) a bottoms liquid containing acetonitrile, water, an amide compound, and an oxazoline compound. In a case where the anthraquinone compound is used in the reaction step, the bottoms liquid further contains the anthraquinone compound. The crude propylene oxide is then purified by a known method or another method in conformity therewith.

The number of the theoretical trays of the first distillation column is generally in a range from 1 to 200. The distillation is generally carried out under the following conditions: a temperature in a range from 0° C. to 300° C., a pressure in a range from 0.005 to 10 MPa, and a reflux ratio in a range from 0.001 to 10. The bottoms liquid, obtained by the distillation of the first distillation column, which liquid mainly includes acetonitrile, water, an amide compound, and an oxazoline compound (plus an anthraquinone compound, if used in the reaction), may be, for example, fed into a second distillation column and further distilled therein; this provides (i) an acetonitrile-water azeotropic mixture from a column top and (ii) a bottoms liquid composed mainly of water, an amide compound, and an oxazoline compound (plus an anthraquinone compound, if used in the reaction). The number of the theoretical trays of the second distillation column is generally in a range from 1 to 100. The second distillation column is generally carried out under the following conditions: a temperature in a range from 0° C. to 300° C., a pressure in a range from 0.005 to 10 MPa, and a reflux ratio in a range from 0.001 to 10.

The bottoms liquid of the second distillation column may be, for example, fed into a third distillation column, which is evaporator, so that the bottoms liquid is further condensed. The third distillation column is generally operated under the following conditions: a temperature in a range from 0° C. to 300° C., a pressure in a range from 0.005 to 10 MPa, and a reflux ratio in a range from 0.001 to 10. Such condensation causes the anthraquinone compound to crystallize; this allows recovery of the anthraquinone compound. The anthraquinone compound thus recovered may include one or more selected from the group consisting of water, acetonitrile, an anthracene compound, an anthrahydroquinone compound, a tetrahydroanthraquinone compound, an amide compound ethylene glycol, dipropylene glycol, tripropylene glycol, and polypropylene glycol.

Examples of the anthracene compound encompass 2-ethylanthracene, 2-t-butylanthracene, 2-amylanthracene, 2-methylanthracene, 2-butylanthracene, 2-t-amylanthracene, 2-isopropylanthracene, 2-s-butylanthracene, 1,3-diethylanthracene, 2,3-dimethylanthracene, 1,4-dimethylanthracene, 2,7-dimethylanthracene, and 2,6-dihydroxylanthracene.

Examples of the anthrahydroquinone compound encompass anthrahydroquinone, 2-ethylanthrahydroquinone, 2-t-butylanthrahydroquinone, 2-amylanthrahydroquinone, 2-methylanthrahydroquinone, 2-butylanthrahydroquinone, 2-t-amylanthrahydroquinone, 2-isopropylanthrahydroquinone, 2-s-butylanthrahydroquinone, 2-s-amylanthrahydroquinone, 2-hydroxyanthrahydroquinone, 1,3-diethylanthrahydroquinone, 2,3-dimethylanthrahydroquinone, 1,4-dimethylanthrahydroquinone, 2,7-dimethylanthrahydroquinone, and 2,6-dihydroxyanthrahydroquinone.

Examples of the tetrahydroanthraquinone compound encompass tetrahydroanthraquinone, tetrahydro-2-ethylanthraquinone, tetrahydro-2-t-butylanthraquinone, tetrahydro-2-amylanthraquinone, tetrahydro-2-methylanthraquinone, tetrahydro-2-butylanthrahydroquinone, tetrahydro-2-t-amylanthraquinone, tetrahydro-2-isopropylanthraquinone, tetrahydro-2-s-butylanthraquinone, tetrahydro-2-s-amylanthraquinone, tetrahydro-2-hydroxyanthraquinone, tetrahydro-1,3-diethylanthraquinone, tetrahydro-2,3-dimethylanthraquinone, tetrahydro-1,4-dimethylanthraquinone, tetrahydro-2,7-dimethylanthraquinone, and tetrahydro-2,6-dihydroxyanthraquinone.

Examples of the amide compound encompass acetamide, N-(2-hydroxypropane-1-yl)acetamide, and N-(1-hydroxypropane-2-yl)acetamide.

A weight ratio of the acetonitrile and the water at a time of the crystallization of the anthraquinone compound may be the same as in a composition of the bottoms liquid of either the second distillation column or the third distillation column; generally, in a range from 0 to 0.5 (acetonitrile to water by weight ratio), and preferably in a range from 0 to 0.1. If necessary, water may be added to the bottoms liquid before the crystallization so that the above ratio of acetonitrile to water is achieved. A method for the crystallization is not particularly limited; for example, cooling crystallization or evaporative crystallization. An upper limit of a crystallization temperature is generally 200° C. or less, and preferably 100° C. or less, in consideration of thermal stability of the anthraquinone compound. A lower limit of the crystallization temperature is 0° C., i.e. a freezing point of water, or greater, and preferably 5° C. or greater. A crystallization pressure is not particularly limited.

Removal of a crystal of the anthraquinone compound obtained as above is typically carried out by filtration. A method for the filtration is not particularly limited; for example, pressure filtration or centrifugal filtration. The crystal may be washed with a mixture of water and a hydrophilic organic solvent after the filtration so that an impurity contained in the crystal is removed. A filtration temperature is generally the same as the crystallization temperature. A filtration pressure is not particularly limited.

The anthraquinone recovered as above may be recycled (i) for use in oxidation in a form of a dry cake after being dried or a wet cake, or (ii) for use in the mixture of solvents which include acetonitrile and water after being dissolved therein or in a slurry form after being mixed therewith. Preferably, it is recycled for use in the mixture of solvents which include acetonitrile and water after being dissolved therein.

The azeotropic composition of the acetonitrile-water mixture, obtained at the column top of the second distillation column, varies depending on the pressure of the distillation column; generally, in a range from (i) 50:50 to (ii) 100:0 (acetonitrile to water by weight ratio). The acetonitrile-water mixture obtained at the column top may be recycled into the reaction step.

The method for producing propylene oxide in accordance with the present invention may include the steps of (i) causing the bottoms liquid, i.e. a mixture of acetonitrile and water, obtained in the distillation step after the gas-liquid separation step, to exchange heat, via a heat exchanger, with the reaction mixture containing the propylene oxide, obtained in the reaction step, (ii) preheating the bottoms liquid under a pressure that is so adjusted that at least part of the bottoms liquid is vaporized at a temperature lower than the reaction temperature of the reaction step, and (iii) azeotropically distilling the bottoms liquid thus preheated, whereby an acetonitrile-water azeotropic mixture is obtained from a column top (hereinafter also referred to as the acetonitrile water).

The heat exchange may be performed with any device. In a case of causing a catalyst to flow with the reaction mixture for the reaction, a coil is provided inside the reactor used in the reaction step, while a jacket is also provided outside the reactor. Further, a crude acetonitrile water is provided in the jacket (hereinafter the crude acetonitrile water refers to the reaction liquid obtained by the gas-liquid separation, in the gas-liquid separation step, of the reaction mixture obtained when the mixture of solvents which include acetonitrile and water is used in the reaction step). Alternatively, the heat exchange may be performed by causing part of the reaction mixture inside the reactor, and the crude acetonitrile water to flow in the heat exchanger provided outside the reactor. Examples of the heat exchanger encompass a shell-and-tube-type heat exchanger, a plate-type heat exchanger, a block-type heat exchanger, and a kettle-type heat exchanger. In a case of using, for example, a fixed-bed reactor similar to the shell-and-tube-type heat exchanger in the reaction step, it may be arranged such that a tube of the reactor is filled with the catalyst, and that materials for the reaction are fed into the tube for the reaction. The crude acetonitrile water is then flowed outside the tube, whereby the heat exchange is performed. Conversely, the heat exchange may be performed by causing the crude acetonitrile water to flow inside a tube and feeding the material for the reaction into a space outside the tube which space is filled with the catalyst. Another method involving use of the fixed-bed reactor is as follows: a tank filled with the catalyst and the heat exchanger are disposed alternately. The reaction mixture is flowed in one side in the heat exchanger, and the crude acetonitrile water is flowed in another side therein. The materials for the reaction are flowed in the tank filled with the catalyst, whereby the reaction causes an increase in temperature of the reaction mixture. The heat exchange is thereby performed between the reaction mixture and the crude acetonitrile water.

Preheating of the crude acetonitrile water as described above before the distillation thereof to be performed in the distillation column decreases a heat amount necessary at the column bottom. The preheating of the reaction mixture does not necessarily need to be accompanied by evaporation thereof; yet, the accompaniment of such evaporation reduces an increase in temperature of the reaction mixture per heat amount exchanged. This advantageously facilitates use of reaction heat in a step of epoxidation. The reaction mixture, which is partly liquid and partly vapor due to evaporation caused by the preheating, may be fed into the distillation column after being separated into a gas phase and a liquid phase; alternatively, it may be fed in the gas-liquid mixed-phase state as it is.

The preheating is performed under the pressure that is so adjusted that the bottoms liquid is vaporized at a temperature lower than the reaction temperature in the reaction step. The preheating is carried out with the heat exchanger coupled with the distillation apparatuses of the azeotropic distillation step described below, via a valve and/or an orifice plate, for example. The pressure in the preheating is maintained to be equal to or lower than the azeotropic distillation. The pressure is generally in a range from 5 kPa to 120 kPa, and preferably in a range from 30 kPa to 100 kPa. The pressure adjusted in the range enables the evaporation of at least part of the crude acetonitrile water at the temperature lower than the reaction temperature in the reaction step.

The azeotropic distillation step is performed after the crude acetonitrile water, at least part of which is vapor, is fed into the second distillation column. The second distillation column may be a heat integrated system, in which multiple distillation columns are combined. The azeotropic distillation step provides the acetonitrile-water azeotropic mixture at the column top, and a liquid containing the water (plus the anthraquinone compound, if used in the reaction) at the column bottom. The composition of the acetonitrile-water azeotropic mixture at the column top varies depending on the pressure of the second distillation column. The pressure thereof is generally in the range from 5 kPa to 10 MPa, and preferably in a rage from 20 kPa to 5 MPa. The azeotropic composition is, for example: in a range from (i) 95:5 to (ii) 50:50 (acetonitrile to water by weight ratio) when the pressure of the second distillation column is in the range from 5 kPa to 10 MPa; and in a range from (iii) 90:10 to (iv) 60:40 (acetonitrile to water by weight ratio) when the pressure of the second distillation column is in the range from 20 kPa to 5 Mpa. The acetonitrile-water azeotropic mixture obtained as above is recycled for use in the reaction step.

When the bottoms liquid to be fed into the second distillation column has a weight ratio (acetonitrile to water) that is larger than the weight ratio of the acetonitrile-water azeotropic mixture, all the water is distilled off to the column top. In this case, the bottoms liquid of the second distillation column is composed mainly of the acetonitrile. The acetonitrile is not a preferable crystallization solvent because solubility of the anthraquinone compound is high in the acetonitrile. Thus, in this case, the crystallization is preferably performed after water is added to the column bottom liquid as a poor solvent. The water may be added in advance in the reaction step, in the gas-liquid separation step, or in the distillation step. It is preferable that part or all of water byproduced in the reaction be utilized as an adding water in advance; alternatively, a filtrate obtained by the filtration of the anthraquinone compound may be utilized as an adding water in advance.

The pressure of the second distillation column is preferably so adjusted that the weight ratio (acetonitrile to water) of the acetonitrile-water azeotropic mixture is lower than a weight ratio (acetonitrile to water) of the crude acetonitrile water to be fed into the second distillation column. For example, when the weight ratio (acetonitrile to water) of the crude acetonitrile water to be fed into the second distillation column is 95:5, the pressure of the second distillation column is preferably 5 kPa or less. When the weight ratio is 90:10, the pressure is preferably 20 kPa or less. When the weight ratio is 80:20, the pressure is preferably 100 kPa or less. When the weight ratio is 70:30, the pressure is preferably 1 MPa or less. When the weight ratio is 60:40, the pressure is preferably 5 MPa or less. When the weight ratio is 50:50, the pressure is preferably 10 MPa. The bottoms liquid of the second distillation column preferably has a weight ratio (acetonitrile to water) in the range from 0 to 0.5, and preferably in the range from 0 to 0.1. At least part of water generated in the reaction step can be removed by disposal of the bottoms liquid.

The acetonitrile-water mixture thus obtained may be recycled in the reaction step. The acetonitrile-water mixture to be recycled is preferably used for dissolution of the anthraquinone compound and/or the ammonium salt. In the case of causing the catalyst to flow with the reaction mixture for the reaction, the catalyst is preferably fed into the reaction step after being suspended in the acetonitrile-water mixture. A temperature of the acetonitrile-water mixture to be recycled may be adjusted to a predetermined temperature. The acetonitrile-water mixture may also be recycled in dissolving a gas that results from recovery of at least part of a desired object such as the propylene oxide, from a gas discharged in the gas-liquid separation step and in the distillation step.

EXAMPLES

The present invention is described below referring to examples; yet, the present invention is not limited to these examples.

Referential Example 1

In a 500 cc autoclave, (i) 131 g of water-acetonitrile solvent (water:acetonitrile=20:80 by weight ratio), (ii) 0.66 g of a Ti-MWW catalyst, and (iii) 0.075 g of an activated carbon catalyst supporting 0.96% of palladium were charged. Then, a pressure in the autoclave was kept at 0.8 MPa (absolute pressure) with nitrogen, while a temperature inside the autoclave was kept at 60° C. by circulating hot water in a jacket of the autoclave. Subsequently, (i) 19.3 Nl/h of a mixture of gases containing: 10.5% by volume of hydrogen; 3.8% by volume of oxygen; 81.5% by volume of nitrogen; and 4.3% by volume of propylene containing 0.44% by volume of propane, and (ii) 89 g/h of acetonitrile-water solvent (water:acetonitrile=20:80 by weight ratio) containing 0.7 mmol/kg of anthraquinone and 0.7 mmol/kg of ammonium dihydrogenphosphate, were continuously fed into the autoclave. The temperature and the pressure were maintained at 60° C. and 0.8 MPa respectively during the reaction. The Ti-MWW catalyst and the palladium-supporting activated carbon catalyst, both being in a solid phase, were filtered with use of a sintered filter. A liquid and a gas discharged from the reactor in a mixed form were separated in a gas-liquid separation tank cooled by a −5° C. jacket. After the pressure was set back to an atmospheric pressure, the gas and the liquid were withdrawn separately in a continuous manner. Starting from 4.5 hours after, the liquid was withdrawn for 25.5 hours, whereby 1,382 g of such liquid was obtained. A composition thereof was as follows: 0.68 wt % of propylene oxide, 0.06 wt % of propylene glycol, and 78 wt % of acetonitrile.

Example 1

Batch distillation of 1,338 g out of 1,382 g of the liquid obtained in Referential Example 1, in a 20-stage distillation column under an atmospheric pressure, resulted in 18.42 g of crude propylene oxide at a column top. The distillation continued thereafter provided 320 g of a mixture liquid composed mainly of acetonitrile at the column top. Then, simple distillation was performed after addition of 50.6 g of ion-exchange water, whereby 931 g of distillate liquid was obtained. Although a solid was precipitated out by this stage, the liquid remaining in the tank was cooled down to 5° C. for further precipitation. Subsequently, the liquid was filtered, whereby anthraquinone cake was obtained. The cake weighed 0.13 g after being dried under a reduced pressure. A liquid chromatographic analysis thereof showed 99.3% by area percentage method (column: L-column ODS, 4.6 mm Φ×15 cm; mobile phase: liquid A (water:acetonitrile=9:1), liquid B (acetonitrile); column temperature: 40° C.; compositional change in mobile phase: the liquid B content was initially 10% for 10 minutes, then was gradually changed to 90% over 40 minutes, and then maintained for 10 minutes; detector: UV254 nm; flow rate of the mobile phases: 1 ml/min).

Referential Example 2

In a 300 cc autoclave, (i) 131 g of acetonitrile-water solvent (acetonitrile:water=80:20 by weight ratio), (ii) 2.28 g of a Ti-MWW catalyst, and (iii) 1.06 g of an activated carbon catalyst supporting 1% of palladium were charged. Then, a pressure in the autoclave was kept at 4 MPa (absolute pressure) under nitrogen atmosphere, while a temperature inside the autoclave was kept at 50° C. by circulating hot water in a jacket of the autoclave. Subsequently, (i) 154.8 Nl/h of a mixture of gases containing: 3.1% by volume of hydrogen; 8.3% by volume of oxygen; and 88.6% by volume of nitrogen, (ii) 87.4 g/h of acetonitrile-water solvent (acetonitrile:water=80:20 by weight ratio) containing 0.7 mmol/kg of anthraquinone and 0.7 mmol/kg of ammonium dihydrogenphosphate, and (iii) 32.6 g/h of propylene liquid containing 0.4% by volume of propane, were continuously fed into the autoclave. The temperature and the pressure were maintained at 50° C. and 4 MPa respectively during the reaction. The Ti-MWW catalyst and the palladium-supporting activated carbon catalyst, both being in a solid phase, were filtered with use of a sintered filter. A liquid and a gas from the reaction were continuously withdrawn at a rate of 115.5 g/h and 215.7 g/h respectively. A liquid and a gas of the reaction were withdrawn simultaneously. After the pressure was set back to an atmospheric pressure, the liquid and the gas discharged from the reactor in a mixed form were separated a liquid and a gas. A composition of each of the liquid and the gas was analyzed by gas chromatography. A result of the analysis showed that the reaction generated 3.77 g/h of propylene oxide, 0.0080 g/h of acetamide, 0.0044 g/h of a mixture of N-(2-hydroxypropane-1-yl)acetamide and N-(1-hydroxypropane-2-yl)acetamide, and 0.0065 g/h of a mixture of 2,4-dimethyloxazoline and 2,5-dimethyloxazoline, and that 27.8 g/h of the propylene, 1.75 nl/h of the hydrogen, and 10.8 nl/h of the oxygen remained unreacted.

Example 2

Gas-liquid separation simulation is performed on the liquid and the gas, withdrawn from the reactor, which is obtained in Referential Example 2 at 50° C. and 0.1 MPa. The reaction liquid has a composition shown in Table 1 below. The liquid having such a composition is fed into a 60th stage of the first distillation column, of which the number of theoretical tray is 100, and distilled at 2 MPa, at a reflux ratio of 3, and at a distillation rate of 3 g/h. Table 2 shows a composition of a liquid at a column top and at a column bottom of the first distillation column. Then, the column bottom liquid of the first distillation column is fed into a 15th stage of the second distillation column, of which the number of theoretical tray is 30, and distilled at 0.1 MPa, at a reflux ratio of 3, and at a distillation rate of 51 g/h. Table 3 shows a composition of a liquid at a column top and at a column bottom of the second distillation column. Further, the column bottom liquid of the second distillation column is fed into a 21st stage of the third distillation column, of which the number of theoretical tray is 40, and distilled at 0.1 MPa, at a reflux ratio of 3, and at a distillation rate of 29 g/h. Table 4 shows a composition of a liquid at a column top and at a column bottom of the third distillation column.

TABLE 1

| Composition | Composition of Liquid [g/h] |
|---|---|
| Propylene | 4.052 |
| Propane | 0.076 |
| Propylene oxide | 2.881 |
| Acetonitrile | 67.02 |
| Water | 20.311 |
| Propylene glycol | 0.373 |
| Hydrogen | 0.002 |
| Oxygen | 0.04 |
| Nitrogen | 0.106 |
| Anthraquinone | 0.012739 |
| Ammonium dihydrogenphosphate | 0.007895 |
| Acetamide | 0.008 |
| Mixture of 2,4-dimethyloxazoline and 2,5-dimethyloxazoline | 0.006 |
| Mixture of N-(2-hydroxypropan-1-yl)acetamide and N-(1-hydroxypropan-2-yl)acetamide | 0.004 |

TABLE 2

| Composition | Composition of bottoms liquid [g/h] | Composition of distillate liquid [g/h] | Gas [g/h] |
|---|---|---|---|
| Propylene | 0 | 3.076 | 0.976 |
| Propane | 0 | 0.058 | 0.018 |
| Propylene oxide | 0 | 2.769 | 0.112 |
| Acetonitrile | 66.488 | 0.521 | 0.011 |
| Water | 19.999 | 0.306 | 0.006 |
| Propylene glycol | 0.373 | 0 | 0 |
| Hydrogen | 0 | 0 | 0.001 |
| Oxygen | 0 | 0.002 | 0.037 |
| Nitrogen | 0 | 0 | 0.106 |
| Anthraquinone | 0.012739 | 0 | 0 |
| Ammonium dihydrogenphosphate | 0.007895 | 0 | 0 |
| Acetamide | 0.008 | 0 | 0 |
| Mixture of 2,4-dimethyloxazoline and 2,5-dimethyloxazoline | 0.006 | 0 | 0 |
| Mixture of N-(2-hydroxypropan-1-yl)acetamide and N-(1-hydroxypropan-2-yl)acetamide | 0.004 | 0 | 0 |

TABLE 3

| Composition | Composition of bottoms liquid [g/h] | Composition of distillate liquid [g/h] |
|---|---|---|
| Propylene | 0 | 0 |
| Propane | 0 | 0 |
| Propylene oxide | 0 | 0 |
| Acetonitrile | 24.355 | 42.132 |
| Water | 11.132 | 8.868 |
| Propylene glycol | 0.373 | 0 |
| Hydrogen | 0 | 0 |
| Oxygen | 0 | 0 |
| Nitrogen | 0 | 0 |
| Anthraquinone | 0.012739 | 0 |
| Ammonium dihydrogenphosphate | 0.007895 | 0 |
| Acetamide | 0.008 | 0 |

TABLE 3-continued

| Composition | Composition of bottoms liquid [g/h] | Composition of distillate liquid [g/h] |
|---|---|---|
| Mixture of 2,4-dimethyloxazoline and 2,5-dimethyloxazoline | 0.006 | 0 |
| Mixture of N-(2-hydroxypropan-1-yl)acetamide and N-(1-hydroxypropan-2-yl)acetamide | 0.004 | 0 |

TABLE 4

| Composition | Composition of Liquid at column bottom [g/h] | Composition of Liquid at column top [g/h] |
|---|---|---|
| Propylene | 0 | 0 |
| Propane | 0 | 0 |
| Propylene oxide | 0 | 0 |
| Acetonitrile | 0.067 | 24.288 |
| Water | 6.02 | 5.112 |
| Propylene glycol | 0.373 | 0 |
| Hydrogen | 0 | 0 |
| Oxygen | 0 | 0 |
| Nitrogen | 0 | 0 |
| Anthraquinone | 0.012739 | 0 |
| Ammonium dihydrogenphosphate | 0.007895 | 0 |
| Acetamide | 0.008 | 0 |
| Mixture of 2,4-dimethyloxazoline and 2,5-dimethyloxazoline | 0.006 | 0 |
| Mixture of N-(2-hydroxypropan-1-yl)acetamide and N-(1-hydroxypropan-2-yl)acetamide | 0.004 | 0 |

Example 3

The following explains a series of steps of the reaction in accordance with the present invention, with reference to a flowchart in FIG. 1 and an example of a material balance in Table 5.

Fed into a reactor (A) are: 1.72 T/h of a solution of hydrogen peroxide (fluid number 1); 71.77 T/h of propylene (fluid number 2); and 10.31 T/h of a mixture solvent of water and acetonitrile (fluid numbers 3 and 13). The hydrogen peroxide and the propylene are allowed to react with each other at a pressure of 1.5 MPa, in the presence of a titanosilicate catalyst, whereby 1.0 T/h of propylene oxide is generated. Heat generated in the reaction is removed by cooling part (fluid number 5) of a reaction mixture by circulating such a part through a heat exchanger (B) provided outside the reactor, whereby a reaction temperature inside the reactor is maintained at 60° C. At this stage, a slight amount of an inert gas (fluid number 4) such as oxygen generated by decomposition of the hydrogen peroxide is purged from the reactor. Then, 13.78 T/h of the reaction mixture (fluid number 6) obtained as above is fed into a gas-liquid separator (C). Distillation of the reaction mixture provides 1.04 T/h of a gas (fluid number 7) composed mainly of propylene at a column top, and 12.74 T/h of a mixture (fluid number 8) of propylene oxide, acetonitrile, and water at a column bottom. The gas composed mainly of the propylene is compressed by a compressor (G), and then recycled in the epoxidation step in combination with 0.73 T/h of propylene (fluid number 2) fed from the outside. The mixture of propylene oxide, acetonitrile, and water obtained as above is fed into a first distillation column (D). Distillation of the mixture produced 1.00 T/h of propylene oxide (fluid number 9) at a column top, and 11.74 T/h of a mixture (fluid number 10) of acetonitrile and water at a column bottom. The mixture of acetonitrile and water thus obtained is decompressed by a pressure control valve (E) so as to have a pressure of 0.033 MPa, and then fed into the heat exchanger (B). Under such a pressure, the mixture of acetonitrile and water forms an azeotropic mixture having a weight ratio of 85 to 15, and would start to evaporate at a temperature in the order of 47° C. The reaction mixture of the epoxidation step, having a temperature of 60° C., is fed into the heat exchanger as a high-temperature fluid. Subsequently, heat exchange is performed and the evaporation of the acetonitrile and the water was thereby caused to continue, whereby 3.45 T/h of a mixture vapor of acetonitrile and water and 8.29 T/h of an unvaporized mixture liquid are obtained. In the above heat exchanger, heat equivalent to 757 kW per ton of propylene oxide (fluid number 9) was exchanged. The mixture vapor of acetonitrile and water and the unvaporaized mixture liquid thus obtained are fed into a second distillation column (F), having a column top at which a pressure was maintained at 0.03 MPa, whereby 10.30 T/h of a mixture (fluid number 13) of acetonitrile and water and 1.44 T/h of water (fluid number 14), from which the acetonitrile have been removed, is obtained, respectively at a column top and at a column bottom. The mixture of acetonitrile and water thus obtained is condensed by a condenser, and compressed by a pump (I). The mixture is then recycled in the epoxidation step in combination with a slight amount of acetonitrile (fluid number 3) fed from the outside.

TABLE 5

| | Fluid number | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Temperature (° C.) | 25 | 25 | 25 | 60 | 55 | 60 | −23 | 86 | 46 | 83 | 47 | 41 | 46 | 70 |
| Pressure (MPa) | 1.60 | 1.60 | 1.60 | 1.50 | 2.00 | 1.50 | 0.19 | 0.20 | 0.15 | 0.16 | 0.033 | 0.033 | 1.600 | 0.031 |
| Flow Rate (T/h) | 1.72 | 0.73 | 0.01 | 0.02 | 189.26 | 13.78 | 1.04 | 12.74 | 1.00 | | 11.74 | | 10.30 | 1.44 |
| Ratio of vapor (wt %) | 0.0 | 0.0 | 0.0 | 100.0 | 0.0 | 0.0 | 100.0 | 0.0 | 0.0 | 0.0 | 15.1 | 29.4 | 0.0 | 0.0 |
| Weight percentage* (wt %) | | | | | *composition of whole fluid | | | | | | | | | |
| Propylene | | 100.0 | | | 9.4 | 7.4 | 7.4 | 98.0 | | | 0.1 | | | |
| Propylene oxide | | | | | 7.4 | 7.4 | 2.0 | 7.8 | 99.9 | | | | | |

TABLE 5-continued

| | Fluid number | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Hydrogen peroxide | 36.0 | | | | | | | | | | | | | |
| Water | 64.0 | | | | 21.6 | 21.6 | trace | 23.4 | trace | | 25.4 | | 15.0 | 99.5 |
| Acetonitrile | | | 100.0 | | 63.5 | 63.5 | | 68.7 | trace | | 74.6 | | 85.0 | 10 ppm |
| Propylene glycol | | | | | | | | 0.1 | | | 0.1 | | | 0.5 |
| Inert gas (oxygen and the like) | | | | 90.6 | | | | | | | | | | |
| Total | 100.0 | 100.0 | 100.0 | 100.0 | 100.0 | 100.0 | 100.0 | 100.0 | 100.0 | | 100.0 | | 100.0 | 100.0 |

Referential Example 3

In a 300 cc autoclave, (i) 131 g of acetonitrile-water solvent (acetonitrile:water=80:20 by weight ratio), (ii) 2.28 g of a Ti-MWW catalyst, and (iii) 1.06 g of an activated carbon catalyst supporting 1% of palladium were charged. Then, a pressure in the autoclave was kept at 4 MPa (absolute pressure) under nitrogen atmosphere, while a temperature inside the autoclave was kept at 50° C. by circulating hot water in a jacket of the autoclave. Subsequently, (i) 154.8 Nl/h of a mixture of gases containing: 3.1% by volume of hydrogen; 8.3% by volume of oxygen; and 88.6% by volume of nitrogen, (ii) 87.4 g/h of acetonitrile-water solvent (acetonitrile:water=80:20 by weight ratio) containing 0.7 mmol/kg of anthraquinone and 0.7 mmol/kg of ammonium dihydrogenphosphate, and (iii) 32.6 g/h of propylene liquid containing 0.4% by volume of propane, were continuously fed into the autoclave. The temperature and the pressure were maintained at 50° C. and 4 MPa respectively during the reaction. The Ti-MWW catalyst and the palladium-supporting activated carbon catalyst, both being in a solid phase, were filtered with use of a sintered filter. A liquid and a gas from the reaction were continuously withdrawn at a rate of 108 g/h and 215 g/h respectively. A liquid and a gas of the reaction were withdrawn simultaneously. After the pressure was set back to an atmospheric pressure, the liquid and the gas were separated. A composition of each of the liquid and the gas was analyzed by gas chromatography. A result of the analysis showed that the reaction generated 3.77 g/h of propylene oxide, 0.373 g/h of propylene glycol, and 0.759 g/h of propane, and that 27.8 g/h of the propylene, 1.75 nl/h of the hydrogen, and 10.8 nl/h of the oxygen remained unreacted.

Example 4

Gas-liquid separation simulation performed on the liquid and the gas withdrawn from the reactor, which is obtained in Referential Example 3, at 2 MPa resulted in 67 g/h of liquefied acetonitrile and 20 g/h of water. A weight ratio of the acetonitrile to the water is 77 to 23. The liquid having such a composition is fed into a 15th stage of a distillation column, of which the number of theoretical tray is 30, and simulation is performed at 0.1 MPaA and at a reflux rate of 3. The simulation shows that an azeotropic composition is realized by an acetonitrile-to-water weight ratio of 83 to 17. At a column top, 50 g/h of an acetonitrile-water mixture liquid having a weight ratio of 83 to 17 is obtained, while 36.9 g/h of a mixture liquid of acetonitrile and water having a weight ratio of 69 to 31 was obtained at a column bottom.

The method of the present invention enables industrially efficient production of propylene oxide by recovery of acetonitrile or a mixture of solvents which include acetonitrile and water for use in the production of propylene oxide from hydrogen peroxide and propylene.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

The invention claimed is:

1. A method for producing propylene oxide, comprising the steps of:
    reacting hydrogen peroxide with propylene either in an acetonitrile solvent or in a mixture of solvents which include acetonitrile and water, in presence of a titanosilicate catalyst, so as to obtain a reaction mixture containing propylene oxide;
    separating the reaction mixture obtained in the reacting into a gas and a reaction liquid; and
    distilling the reaction liquid obtained in the separating, so as to separate the reaction liquid into a distillate liquid containing propylene oxide, and a bottoms liquid including acetonitrile or a combination of acetonitrile and water,
    wherein the hydrogen peroxide is produced by reaction of oxygen and hydrogen, in presence of (i) a palladium catalyst supported on a carrier and (ii) an anthraquinone compound, within a reaction system of the reacting.

2. The method for producing propylene oxide according to claim 1, wherein the bottoms liquid contains an anthraquinone compound.

3. The method for producing propylene oxide according to claim 2, further comprising the steps of:
    distilling the bottoms liquid so that the acetonitrile solvent or the mixture of solvents which include acetonitrile and water is removed; and
    crystallizing the anthraquinone compound in the bottoms liquid so that the anthraquinone compound is separated out.

4. The method for producing propylene oxide according to claim 1, wherein the bottoms liquid contains an amide compound and an oxazoline compound, the amide compound and the oxazoline compound being generated in the reacting as byproducts.

5. The method for producing propylene oxide according to claim 4, wherein the amide compound is acetamide, N-(2-hydroxypropan-1-yl)acetamide, or N-(1-hydroxypropan-2-yl)acetamide.

6. The method for producing propylene oxide according to claim 4, wherein the oxazoline compound is 2,4-dimethyloxazoline or 2,5-dimethyloxazoline.

7. The method for producing propylene oxide according to claim 4, further comprising the step of:
distilling the bottoms liquid containing the amide compound and the oxazoline compound, so as to distill off an acetonitrile-water azeotropic mixture from a column top and an aqueous phase containing the amide compound and the oxazoline compound at a column bottom.

8. The method for producing propylene oxide according to claim 1, further comprising the step of:
performing heat-exchange via a heat-exchanger between the bottoms liquid, which is a mixture of acetonitrile and water, obtained in the step of distilling after the step of separating, and with the reaction mixture containing the propylene oxide, obtained in the step of reacting;
preheating the bottoms liquid under a pressure that is so adjusted that at least part of the liquid is vaporized at a temperature lower than a reaction temperature in the reacting; and
azeotropically distilling at least the part of the bottoms liquid thus preheated, so as to obtained an azeotropic mixture of acetonitrile and water from the column top.

9. The method for producing propylene oxide according to claim 8, wherein the preheating of the column bottom liquid is performed under a pressure in a range from 5 kPa to 120 kPa.

10. The method for producing propylene oxide according to claim 8, wherein the preheating of the column bottom liquid is performed under a pressure in a range from 30 kPa to 100 kPa.

11. The method for producing propylene oxide according to claim 8, wherein a pressure in the step of azeotropic distilling is in a range from 5 kPa to 10 MPa.

12. The method for producing propylene oxide according to claim 8, wherein a pressure in the step of azeotropic distilling is in a range from 20 kPa to 5 MPa.

13. The method for producing propylene oxide according to claim 1, wherein the palladium catalyst supported on the carrier is a titanosilicate catalyst that supports palladium.

14. The method for producing propylene oxide according to claim 1, wherein the titanosilicate catalyst has a 12 or more-membered oxygen ring pore.

15. The method for producing propylene oxide according to claim 14, wherein the titanosilicate catalyst having a 12 or more-membered oxygen ring pore is crystalline titanosilicate having MWW structure or a precursor thereof.

16. The method for producing propylene oxide according to claim 1, wherein the carrier of the palladium catalyst comprises is activated carbon.

\* \* \* \* \*